(12) United States Patent
O'Shea et al.

(10) Patent No.: US 9,149,050 B2
(45) Date of Patent: Oct. 6, 2015

(54) USE OF CONJUGATED LINOLEIC ACID

(75) Inventors: Marianne O'Shea, Channahon, IL (US); Chryssanthi Stylianopoulos, Veria (GR); Corey Edison Scott, Channahon, IL (US); Dale A. Schoeller, Madison, WI (US)

(73) Assignee: STEPAN SPECIALTY PRODUCTS, LLC, Wilmington, DE (US)

( * ) Notice: Subject to any disclaimer, the term of this patent is extended or adjusted under 35 U.S.C. 154(b) by 971 days.

(21) Appl. No.: 13/264,707

(22) PCT Filed: Apr. 14, 2010

(86) PCT No.: PCT/EP2010/002280
§ 371 (c)(1),
(2), (4) Date: Mar. 21, 2012

(87) PCT Pub. No.: WO2010/118856
PCT Pub. Date: Oct. 21, 2010

(65) Prior Publication Data
US 2012/0172444 A1  Jul. 5, 2012

(30) Foreign Application Priority Data

Apr. 17, 2009  (EP) .................................. 09251120

(51) Int. Cl.
*A61K 31/20* (2006.01)
*A23C 9/152* (2006.01)
*A23L 1/29* (2006.01)
*A23L 1/30* (2006.01)

(52) U.S. Cl.
CPC .............. *A23C 9/1528* (2013.01); *A23L 1/293* (2013.01); *A23L 1/3008* (2013.01); *A61K 31/20* (2013.01); *A23V 2002/00* (2013.01)

(58) Field of Classification Search
CPC .................................................... A61K 31/20
USPC ................................. 514/560, 549
See application file for complete search history.

(56) References Cited

U.S. PATENT DOCUMENTS 6,440,931 B1 * 8/2002 Remmereit et al. .......... 424/439

FOREIGN PATENT DOCUMENTS

| ES | 2296438 | 4/2008 | ............... A23L 1/30 |
| ES | 2302396 | 7/2008 | ............... A23C 9/13 |
| JP | 3230082 | 11/2001 | |
| WO | WO 96/06605 | 3/1996 | ............. A61K 31/20 |

OTHER PUBLICATIONS

International Search Report dated Apr. 6, 2010 issued in the international application No. PCT/EP2010/002280.
International Preliminary Report on Patentability dated Oct. 27, 2011 issued in the international application No. PCT/EP2010/002280.
S. Einerhand, "New insight: Clarinol™ CLA helps overweight and obese people lose fat where it matters most, Decrease in abdominal fat promotes health and well being", Agrofood Industry Hi-Tech, vol. 17, No. 9, Sep. 2006, pp. 2-3.
M. Moya et al., "Utilización del ácido linoleico conjugado (CLA) en el niño y adolescente obesos", Revista Española De Pediatría, vol. 64, No. 1, Jun. 2007, pp. 89-93.
S. Daniells, "CLA in milk works for weight management-study", [Online] Oct. 16, 2007, pp. 1-1, Retrieved from the Internet: URL:http://www.nutraingredients.com/Research/CLA-in-milk-works-for-weight-management-study.
N. Laso, "Effects of milk supplementation with conjugated linoleic acid (isomers cis-9, trans-11 and trans-10, cis-12) on body composition and metabolic syndrome components", British Journal of Nutrition, Mar. 27, 2007, vol. 98, pp. 860-867.
B. Bonet Serra et al.,: "Efectos de la suplementación con acido linoleico conjugado sobre parámetros relacionados con el metabolismo lipídico y la resistencia a la insulina en niños y adolescentes obesos", Bol Pediatr, vol. 47, no. Supl.1, 2007, pp. 18-22.
S. Daniells, "Obese children may benefit from CLA: study", [Online] Feb. 29, 2008, pp. 1-1, Retrieved from the Internet: URL:http://www.nutraingredients.com/Research/Obese-children-may-benefit-from-CLA-study.
Innovations in Food Technology, "Clarinol™ CLA: What are the possibilities in food", Print Workshop Publications, Burnham, GB, vol. Nov. 1, 2008, pp. 64-65.
Racine et al., "Effect of conjugated linoleic acid on body fat accretion in overweight or obese children," Amer. J. Clin. Nutr., 91(5): 1157-1164 (2010).
Office Action issued in European Patent Application No. 10713852. 1-2114 (2012).

* cited by examiner

Primary Examiner — Raymond Henley, III
(74) Attorney, Agent, or Firm — Barnes & Thornburg LLP (57) ABSTRACT

Conjugated linoleic acid (CLA) or a derivative thereof may be used in reducing the rate of increase of fat mass in a growing child.

32 Claims, 4 Drawing Sheets

USE OF CONJUGATED LINOLEIC ACID

RELATED APPLICATIONS

The present application is a U.S. National Phase Application of International Application No. PCT/EP2010/002280 (filed Apr. 14, 2010) which claims priority to European Application No. 09251120.3 (filed Apr. 17, 2009) which are hereby incorporated by reference in their entirety.

This invention relates to the use of conjugated linoleic acid (CLA). In particular, the invention relates to the use of CLA for a specific use in children.

In recent years, many countries have experienced a significant increase in rates of childhood obesity. Obesity in children can lead to health problems and may have a negative effect on well-being. These problems can persist into adulthood where obesity can present even greater health problems. Obesity may be a contributing factor in the increased incidence of various diseases including coronary artery disease, hypertension, stroke, diabetes and certain cancers.

Obesity in children is frequently assessed in terms of body mass index (BMI). However, with children, the predicted BMI naturally varies with the age of the child. Growth charts published by bodies such as the World Health Organisation at http://www.who.int/growthref/who2007_bmi_for_age/en/index.html and the Centers for Disease Control and Prevention in the United States at http://www.cdc.gov/nchs/about/major/nhanes/growthcharts/clinical_charts.htm show how the average BMI decreases to age about 4 to 7 years in boys and 5 to 7 years in girls and then increases thereafter. Thus, the control of BMI in children is subject to different constraints than in adults.

Conjugated linoleic acid (CLA) is a conjugated dienoic fatty acid having 18 carbon atoms. As a result of the presence of the two double bonds in CLA, geometrical isomerism is possible and the CLA molecule or moiety may exist in a number of isomeric forms. The cis9, trans11 ("c9,t11") and trans10, cis12 ("t10,c12") isomers of CLA are generally the most abundant and beneficial pharmacological effects have been identified for each of these isomers.

CLA has been used to control obesity and reduce BMI in adults. For example, http://www.clarinol.com/CLAInTheNews/News/ResearchConfirms2.asp discloses the results of a clinical trial, in which a group taking CLA showed a marked reduction in waist-to-hip ratio, as well as in overall body weight and BMI, compared to a placebo group.

U.S. Pat. No. 5,554,646 discloses a method of reducing body fat by administering CLA to an animal. Methods of preserving or increasing the animal's body protein by administering the CLA are also disclosed.

U.S. Pat. No. 5,814,663 describes a method of maintaining an existing level of body fat or body weight in a human which comprises administering CLA.

Clarinol™ CLA: What are the possibilities in food, Innovations in Food Technology, Print Workshop Publications, 1 Nov. 2008, pages 64-65 discloses the effect of CLA in reducing body fat mass and increasing lean body mass.

Sandra Einerhand, New insight: Clarinol™ CLA helps overweight and obese people lose fat where it matters most, AgroFOOD industry hi-tech, vol, 17, no 9, September 2006, pages 2-3 describes the effect of CLA in reducing body fat and increasing muscle mass in adults.

Moya et al, Revista Española, de Pediatria, vol 64, no 1, June 2007, pages 89-93 describes a study on the effect of CLA in obese children.

Bonet Serra et al, Bol Pediatr, vol 47, suppl 1, 2007, pages 18-22 reports a study on the effect of CLA in obese adolescents.

ES-A-2296438 and ES-A-2302396 disclose a functional food that comprises a non-fermented milk product and a concentrate of vegetable oil rich in conjugated linoleic acid. The vegetable oil rich in conjugated linoleic acid comprises a 1 to 1 mixture of cis-9, trans-11 isomers and trans-10, cis-12 isomers of conjugated linoleic acid at a proportion exceeding 80 percent by weight with respect to the total weight of the concentrate.

Although CLA has been used in adults for reducing body fat, there is no predictability between adults and children in this regard. Most children naturally undergo a gradual increase in body fat and BMI from age 6 years to 20 years.

DETAILED DESCRIPTION

There remains a need for safe and effective treatments of childhood obesity. In particular, there is a need for treatments that do not involve prescribed medications, some of which have potentially undesirable side effects. There is especially a need for treatments that can form part of a normal diet and that can be effective together with exercise.

Surprisingly, it has been found that CLA can have a positive effect on obesity in children. Unlike in adults, CLA does not reduce fat mass. However, it has been found that in children CLA can reduce the relative increase in fat mass with age that is predicted according to growth charts. This result was unexpected because the effect of CLA on a child already experiencing an increase in body fat mass, and BMI, with age, could not have been predicted.

Accordingly, the invention provides conjugated linoleic acid (CLA) or a derivative thereof for use in reducing the rate of increase of fat mass in a growing child.

Also provided by the invention is the use of conjugated linoleic acid or a derivative thereof in the manufacture of a composition for use in reducing the rate of increase of fat mass in a growing child.

Further provided by the invention is a method of reducing the rate of increase of fat mass in a growing child which comprises administering to a child in need thereof an effective amount of conjugated linoleic acid or a derivative thereof.

By the term "growing" child, it is meant that the child has not reached full height and preferably less than 95% or less than 90% of full height. The child will be more than 2 years old and will preferably have an age of from 4 to 18 years, more preferably from 4 to 16 years, such as from 5 to 12 years, even more preferably from 6 to 10 years. The child is preferably of an age at which the BMI for the $50^{th}$ percentile is increasing with age. It will be understood that the child is a human. Preferably, the child is at risk of becoming overweight. The child may be, for example, at least the $85^{th}$ percentile for weight.

Preferably, the CLA or a derivative thereof of the invention is for use in reducing the fat mass as a percentage of total body weight. Thus, the relative proportion of the weight of the body that is provided by fat decreases, although the weight of the child may increase at the same time. Correspondingly, lean tissue mass may increase as a percentage of total body weight.

It is preferred in the invention that abdominal fat mass is reduced as a percentage of total body weight. Leg and/or arm fat may also be reduced.

Methods of determining the fat and lean mass of an individual are well-known in the art.

The CLA or derivative thereof may be used in the invention to reduce the rate of increase in fat mass and/or BMI. The reduction of the increase in this context means that the rate of increase in fat mass and/or BMI that would otherwise be predicted, for example on the basis of the individual's position on the growth charts, such as those mentioned above, is less than expected. Thus, the individual may move to a lower percentile. It will be understood that the fat mass and/or BMI will still increase, but the rate of increase will be reduced.

In the context of this invention, reducing the rate of increase of fat mass in a growing child and/or reducing the rate of increase in BMI preferably include one or more of the following: controlling the fat mass increase in children, reducing the fat mass increase in children, reducing fat mass in children, reducing total fat mass in children, support against obesity in children, support for overweight children, promoting healthy growth in children, promoting healthy BMI development in children and supporting healthy development and weight in children.

It will be appreciated that the CLA or derivative thereof may need to be taken regularly over a period of time of months to years, such for at least 2 months and up to 6 months or up to 1 year, in order for the effects to be observed.

The CLA or derivative thereof that is used in the invention may be in the form of a free acid or a physiologically acceptable salt or ester thereof. Physiologically acceptable salts include sodium salts. Esters include alkyl esters obtainable from alcohols having from 1 to 6 carbon atoms, including monohydric, dihydric, trihydric and polyhydric alcohols. As used herein, an "ester" of CLA includes any and all positional and geometric isomers of CLA bound through an ester linkage to an alcohol or any other chemical group, including but not limited to physiologically acceptable, naturally occurring alcohols (e.g., methanol, ethanol, propanol). Therefore, an ester of CLA or esterified CLA may contain any of the positional and geometric isomers of CLA.

One preferred form of CLA for use in the invention is CLA in the form of a free acid.

An even more preferred form of CLA for use in the invention is CLA in the form of a triglyceride. As used herein, a "triglyceride" of CLA contains CLA at any or all of three positions on the triglyceride backbone. Accordingly, a triglyceride containing CLA may contain any of the positional and geometric isomers of CLA.

The CLA or derivative thereof may comprise a single isomer of CLA or a mixture of two or more different isomers including: cis, cis; cis, trans; trans, cis; and trans, trans isomers. Preferred isomers are the trans10, cis12 and cis9, trans 11 isomers (also referred to herein as t10,c12 and c9,t11, respectively), including these isomers in relatively pure form, as well as mixtures with each other and/or mixtures with other isomers. Typically, the CLA or derivative thereof that is used in the invention will comprise at least 30% by weight of the c9,t11 isomer and/or at least 30% by weight of the t10,c12 isomer based on the total weight of CLA isomers present. More preferably, the CLA or derivative thereof comprises t10,c12 and c9,t11 isomers and the weight ratio of t10,c12 isomer to c9,t11 isomer or vice versa is at least 1.2:1, such as 1.3:1, even more preferably at least 1.5:1, e.g., in the range 1.5:1 to 100:1 or 1.5:1 to 10:1. Particularly preferred are compositions comprising the t10,c12 isomer or the c9,t11 isomer as the major isomer component i.e., present in an amount of at least 55%, preferably at least 60%, more preferably at least 70%, even more preferably at least 75%, most preferably at least 80%, such as at least 90% or even 100% by weight based on the total amount of conjugated linoleic acid. For example, the CLA may comprise c9,t11 and t10,c12 isomers and the weight ratio of the c9,t11 to t10,c12 isomers may be from 99:1 to 1 to 99, preferably from 90:10 to 10:90 most preferably from 80:20 to 20:80.

CLA and its derivatives can be produced in conventional ways. For example, CLA can be produced by known methods, such as that described in EP-A-902082 and WO 99/47135, the contents of each of which are incorporated herein by reference. CLA products that are enriched in one or more isomers are disclosed in WO 97/18320, the contents of which are also incorporated herein by reference.

The CLA or derivative thereof may be used in the invention as the sole fatty acid (i.e., straight chain carboxylic acid having from 12 to 24 carbon atoms) or it may be used in admixture with one of more other fatty acids.

Examples of other fatty acids that may be present in admixture with the CLA or derivative thereof include linoleic acid, oleic acid, pinolenic acid, saturated fatty acids, EPA (eicosapentaenoic) and DHA (docosahexaenoic). These other fatty acids may be present as free acids or derivatives in the same way as CLA and are preferably present as glycerides, more preferably triglycerides.

The CLA or a derivative thereof may be provided for use in the invention in the form of a component of a food product, a pharmaceutical composition or a food supplement. Food products and food supplements are particularly preferred.

Food products (which term also includes beverages) in which the CLA or derivatives thereof can be used include, but are not limited to: margarines; low fat spreads; very low fat spreads; bicontinuous spreads; water continuous spreads; confectionery products, such as chocolates, coatings or fillings; ice creams; ice cream coatings; ice cream inclusions; dressings; mayonnaises; sauces; bakery fats; shortenings; cheese; meal replacement products; health bars; muesli bars; drinks; dairy products; low carbohydrate products; low calorie products; soups; cereals; and milk shakes.

It is particularly preferred that food product comprising the CLA or derivative is in the form of a dairy product. A milk or flavoured milk is most preferred.

Pharmaceutical compositions may, for example, be in the form of tablets, pills, capsules, caplets, multiparticulates including: granules, beads, pellets and micro-encapsulated particles; powders, elixirs, syrups, suspensions and solutions. Pharmaceutical compositions will comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions and syrups. Optionally, the compositions comprise one or more flavouring and/or colouring agents. Pharmaceutically acceptable carriers suitable for use in such compositions are well known in the art of pharmacy. The compositions of the invention may contain 0.1-99% by weight of CLA or derivative. The compositions of the invention are generally prepared in unit dosage form. Preferably, the unit dosage of CLA or derivative is from 1 mg to 1000 mg (more preferably from 100 mg to 750 mg). The excipients used in the preparation of these compositions are the excipients known in the art.

Food supplements (which term includes nutritional products) containing CLA or a derivative thereof are preferably in the form of a soft gel or a hard capsule. Typically, they comprise an encapsulating material, preferably selected from the group consisting of gelatin, glycerol, starch, modified starch, and starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the unit dosage of CLA or derivative of CLA in the food supplement is from 1 mg to 1000 mg (more preferably from 100 mg to 750 mg).

The food products, pharmaceutical compositions and food supplements may contain other additives that are well known in the art of food and pharmaceutical products including, but not limited to, flavouring ingredients, colouring agents, sweeteners and emulsifiers.

The CLA or derivative thereof is typically provided for consumption in an amount of from 0.5 to 5 g per day, more preferably from 1 to 3.5 g per day.

Some of the methods of the invention involve administering the CLA or derivative thereof. By the term "administering", it is not intended necessarily to require the presence of a health professional. The CLA or derivative thereof may simply be provided to the individual for consumption.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise.

EXAMPLE

Summary

A randomized, double blind, placebo-controlled trial was carried out for 6 months.

The subjects were all volunteers and were healthy children (6-10 years old) who were either overweight or at risk of becoming overweight i.e., at the 85th to 98th percentile for height and weight.

The subjects were given 2.4 g/day Clarinol™ or placebo (sunflower oil) in chocolate milk to drink once per day for 6 months. Clarine™ is a CLA triglyceride product that is available from Lipid Nutrition BV, Wormerveer, The Netherlands.

No exercise or diet intervention was implemented. The habitual diet, exercise and adverse events were accessed at baseline and 6 months.

Measurements of fat mass and lean mass were evaluated by dual-energy X-ray absorptiometry (DEXA) after 6 months. Blood was collected at baseline and 6 months for safety measurements.

The baseline characteristics of the subjects were as follows:

|  | Placebo (n = 25) | Clarinol (n = 28) |
| --- | --- | --- |
| Gender | | |
| Male | 15 | 16 |
| Female | 10 | 12 |
| Age (years) | 8.4 ± 0.99 | 8.3 ± 1.1 |
| Height (cm) | 136 ± 7.81 | 138.7 ± 7.78 |
| Weight (kg) | 41.0 ± 7.18 | 44.8 ± 13.5 |
| BMI (Kg/m2) | 22.09 ± 2.57 | 23.2 ± 4.6 |
| % Fat | 31.1 ± 6.0 | 32.7 ± 5.0 |

At the end of the study, the characteristics of the subjects were as follows:

|  | Placebo (n = 25) | Clarinol (n = 28) |
| --- | --- | --- |
| Gender | | |
| Male | 15 | 16 |
| Female | 10 | 12 |
| Age (years) | 9.4 ± 1.1 | 9.1 ± 1.1 |
| Height (cm) | 139 ± 7.35 | 141.0 ± 7.59 |
| Weight (kg) | 44.7 ± 7.78 | 48.0 ± 14.0 |
| BMI (Kg/m2) | 23.18 ± 2.95 | 23.73 ± 4.6 |
| % Fat | 32.4 ± 6.0 | 32.2 ± 5.0 |

The results of the trial are also shown in FIGS. 1 to 4.

Figure 1:
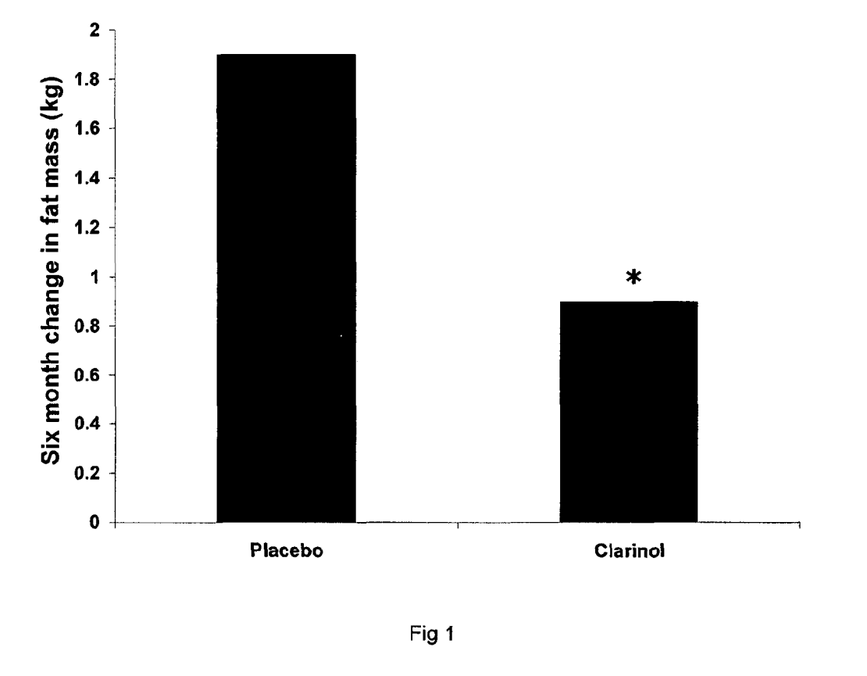
FIG. 1 shows the effect of CLA in reducing the gain in fat mass.

FIG. 1 shows the effect of the CLA (Clarinol™) in reducing the gain in fat mass.

Figure 2:
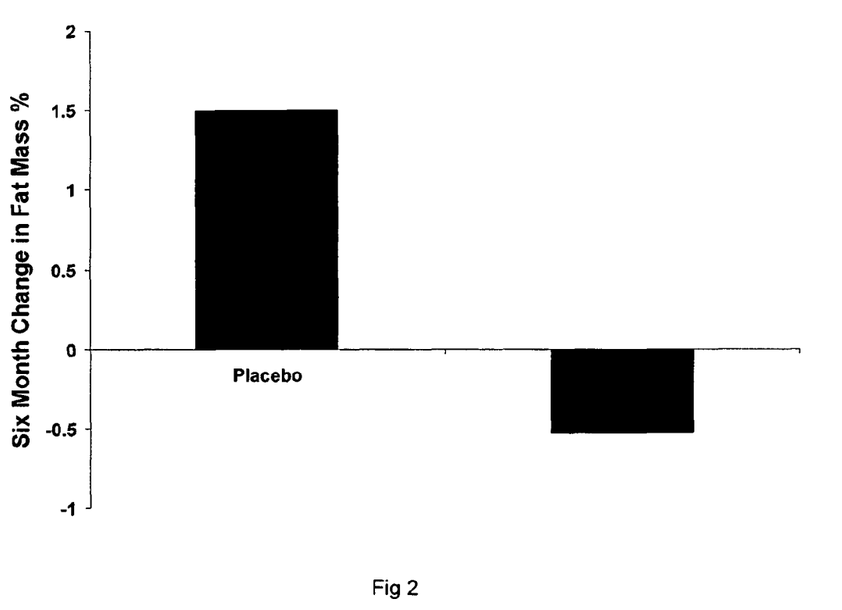
FIG. 2 shows the effect of CLA in reducing fat mass percentage.

FIG. 2 shows the effect of the CLA in reducing fat mass percentage.

Figure 3:
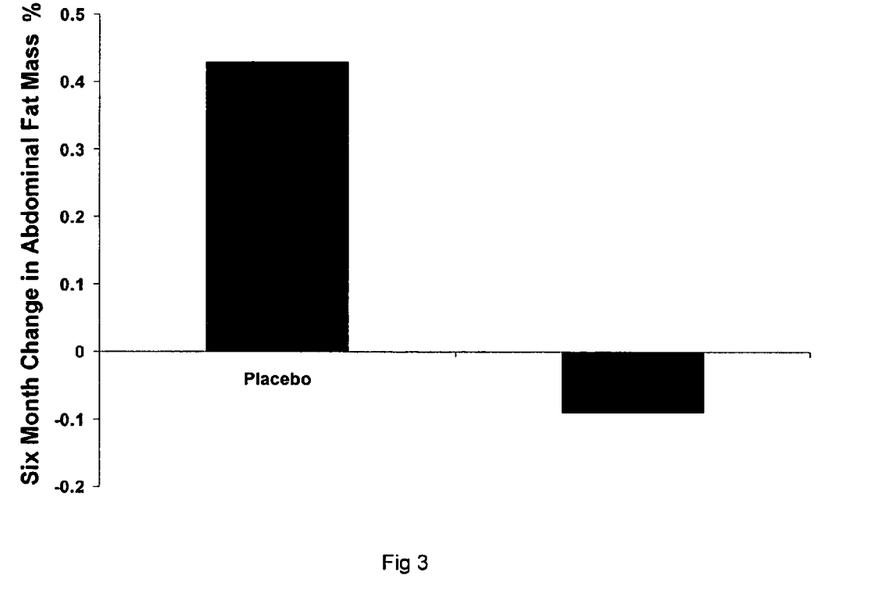
FIG. 3 shows the effect of CLA in reducing abdominal fat mass percentage.

FIG. 3 shows the effect of the CLA in reducing abdominal fat mass percentage.

Figure 4:
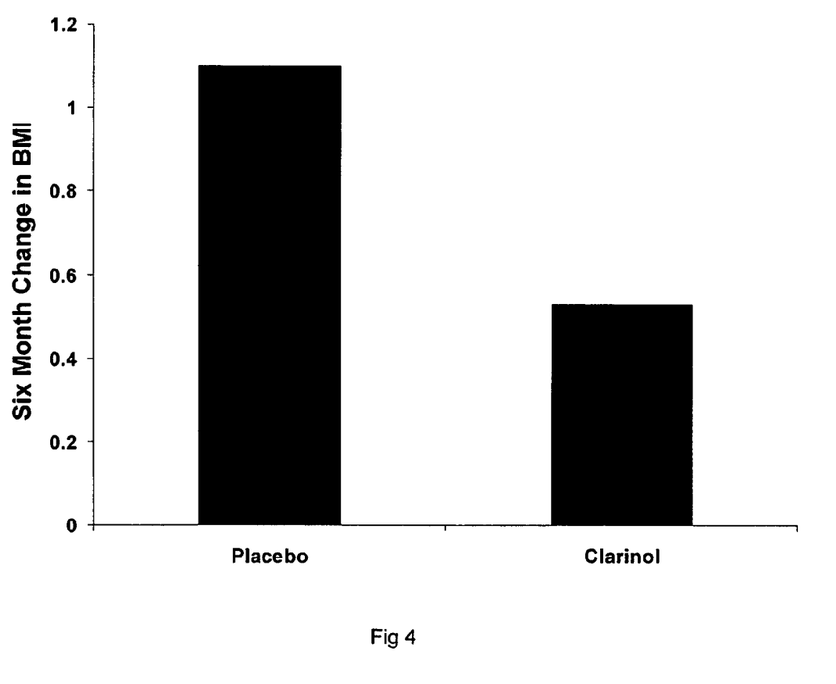
FIG. 4 shows the effect of CLA in reducing increases in body mass index (BMI).

FIG. 4 shows the effect of the CLA in reducing increases in BMI.

The study shows that in children at risk of becoming overweight, CLA significantly: reduces increases in fat mass, reduces increases in fat mass %, reduces increases in abdominal fat mass % and reduces increases in BMI. CLA also shows a strong trend to increase lean tissue mass gain.

All of the observed changes were independent of diet and exercise. All blood parameters remained within the normal range.

Details

The trial is described in more detail in the following:

Methods: A six-month double-blind placebo-controlled human trial was conducted to test the efficacy of CLA in 63 healthy 6-10 year old pre-pubertal children who were overweight ($85^{th}$-$94^{th}$ body mass index (BMI) percentile) or obese ($\geq 95^{th}$ BMI percentile). Subjects were randomized to 3 grams per day of 80% CLA (50:50 cis-9, trans-11 and trans-10, cis-12 isomers in triglyceride form) or placebo (sunflower oil); both treatments were delivered in a reduced fat chocolate milk beverage.

Results: Fifty-three subjects completed the trial and met the a priori compliance rate of 75%. CLA reduced the rate of increase in BMI (0.53±0.83) compared to placebo (1.1±1.1, P=0.05), although there was a trend for greater linear growth in the CLA group compared to placebo (3.4±1.2 vs. 2.8±1.1 cm, P=0.06). Body composition by dual energy x-ray absorptiometry (DXA) showed that CLA reduced body fat percentage compared to placebo (−0.5±2.1 vs. 1.5±1.5%, P=0.0003). Abdominal body fat as a percentage of total body weight was decreased by CLA compared to placebo (−0.09±0.86 vs. 0.43±0.59%, P=0.002). There were no significant changes in plasma glucose, insulin, or low density lipoprotein (LDL) cholesterol. Plasma high density lipoprotein (HDL) cholesterol, however, decreased slightly in the CLA group compared to the placebo group (−5.1±7.3 vs. −0.89±7.9 mg/dL, P=0.05). Reported gastrointestinal symptoms did not differ between groups.

Subjects and Methods

Subjects

Subjects were recruited from the Madison metropolitan area largely through recruitment flyers. Eligible participants were 6-10 year old children with a body mass index (BMI) at or above the 85$^{th}$ percentile at time of screening. The exclusion criteria included: puberty beyond Tanner stage 1, any history of metabolic disease, excessive fear of a blood draw, claustrophobia, and an extreme dislike of the taste of the treatment delivery beverage. Subjects were also excluded if their screening blood chemistries exceeding the following: glucose >110 mg/dL, insulin >45 uIU/mL, LDL >160 mg/dL, total cholesterol >240 mg/dL, triglycerides >200 mg/dL, AST >40 U/L up to 9 yo and females age 10, >50 U/L males age 10, ALT >65 U/L, GGT >30 U/L. The study was approved by the Humans Subjects Committee of the University of Wisconsin-Madison. The study was listed on the Clinical Trials site and is NCT00575991. Parents or guardians signed an informed consent, and subjects signed a minor assent.

The parents of ninety-two subjects indicated willingness to participate and were screened for eligibility. Of the 92 screened subjects, 76 were eligible to participate. Of these 63 (37 boys and 26 girls) agreed to participate and were randomized to CLA or placebo. Subjects were randomized using a stratified design according to gender (M/F), BMI percentile (above/below 95th percentile) and age (above/below 10 years). A priori criteria for completion included consumption of 75% of the milk provided and return for outcome measures at 6 months. There were 55 subjects who completed the study and 53 of these are included in this data analysis. The eight subjects who did not complete included four who grew to dislike the milk delivery vehicle, one who did not consume 75% of the milk in the first 3 months, one who had gastrointestinal problems, one who left the study due to self-esteem issues, and one who could no longer be contacted. The two subjects who were not included in data analysis did to not meet the a priori compliance rate of 75% treatment consumption.

Protocol

During screening, height and weight were measured by University of Wisconsin Hospital (CTRC) nurses and used to calculate BMI for eligibility. Subjects' parents/guardians provided a medical history, and subjects underwent a physical exam during a meeting with a UW Hospital pediatric endocrinologist. A short nutrition education session was held with a CTRC registered dietician.

After passing screening, subjects were seen at the Exercise Science Lab of the UW FitKids Clinic at Sports Medicine.

The baseline body composition visit was approximately two weeks after the screening visit. Body composition was measured by DXA. A baseline symptoms questionnaire was completed by subjects' parents. Subjects were sent to the UW Hospital Lab for blood draw during the period from one week before to one week after the body composition appointment. At 6 months, subjects returned and all the tests performed at baseline were repeated. Milk counts were performed at 3- and 6-months to monitor compliance.

Both the CLA and placebo were added to a skimmed milk to produce a 250 gram chocolate 1.4% fat milk beverage, which was manufactured and packaged by Tetra Pak, Inc (Denton, Tex., USA). The CLA was a 50:50 mix of cis-9, trans-11 and trans-10, cis-12 isomers in triglyceride form with 2.4 g active CLA per serving. It was manufactured from safflower oil by Lipid Nutrition B.V. (Wormerveer, The Netherlands). The placebo was 3 g sunflower oil per serving and was manufactured Tetra Pak, Inc.

Weight, Height, and Body Composition

All measurements were taken under standardized conditions by the same investigators. All participants were asked to void and defecate before beginning the procedures. Height was measured with a wall mounted stadiometer to the nearest 0.5 cm. Weight used for the DXA scan calculations was measured on a calibrated beam balance platform scale to the nearest 0.1 kg with subject wearing only a swim suit or t-shirt and gym shorts.

Body composition was measured on a Norland XR-36 whole body DXA (Norland Corporation, Ft. Atkinson, Wis., USA) and tissue masses were analyzed using software version 3.7.4/2.1.0. The XR-36 x-ray tube operates at 100 kV and uses dynamic samarium filtration (K-edge at 46.8 keV) to produce energy peaks at maximum of 40 and 80 keV. The XR-36 uses dynamic filtration to minimize beam hardening. Dual NaI detectors measure the attenuated x-ray using a pixel size of 6.5×13.0 mm and a scan speed of 260 mm/sec. Based on 18 scans of 6 subjects using the XR-36 whole body procedures the total body coefficients of variation (CV) are as follows: soft tissue mass 0.2%, total body mass 0.2%, lean body mass 1.0%, fat mass 2.5%, percent fat 2.4% and total BMC 0.9%. The XR-36 uses the following calibration standards for determination of bone, fat and lean from x-ray attenuation: bone—hydroxyapatite, fat—steric acid, lean—0.6% NaCl in $H_2O$. All subjects were scanned in the supine position. Subjects removed metal objects or clothing containing metal components and wore only a swim suit or gym shorts and t-shirt for the scan procedure. We used this to determine bone mineral content, body density, percent fat, and abdominal fat mass. Fat mass (FM) was calculated from body weight measured by beam balance times percent fat/100, and fat-free mass (FFM) calculated by difference between FM and weight.

Statistics

The primary outcome variable was the change in body fat percentage as measured by DXA. Between group change was tested with a t-test for comparison of 6-month differences in body composition body mass index (BMI, kg/m$^2$), BMI z-score, FM, FFM and blood chemistries and within group change was tested with a paired t-test using a Student's t-test. Prior to this, the change scores were tested for outliers and measures 3 standard deviations from the mean removed and tested for normality using the Shapiro Wilk test in NCSS 2007 software. Values are presented as the mean and standard deviation. A p value of ≤0.05 was used to identify statistical significance.

Results

Subjects

There were no differences between groups at baseline and no difference between treatment groups with regard gender distribution.

With regard to stratification, there were 5 boys and 9 girls under the 95$^{th}$ percentile for BMI and under 9.5 years of age, 7 boys and 2 girls under the 95$^{th}$ percentile for BMI and at or above 9.5 years of age, 16 boys and 13 girls at or above the 95$^{th}$ percentile for BMI and under 9.5 years of age, and 9 boys and 2 girls at or above the 95$^{th}$ percentile for BMI and at or above 9.5 years of age.

Anthropometrics and Body Composition

There were no significant differences in anthropometric measures at baseline. Similarly, there were no significant changes in body composition at baseline.

CLA treatment did result in several significant differences in anthropometric and body composition measures. Body weight gain did not differ between treatment and placebo (3.2±1.9 vs 3.7±2.2 kg P=0.4). Height increase tended to be greater in the CLA group, however, did not reach significance (3.4±1.2 vs. 2.8±1.1 cm, P=0.06). CLA reduced the increase in BMI (0.54±0.84) compared to placebo (1.1±1.1, P=0.05). When expressed as BMI z-score, the value did trend downward in the CLA group, but was not statistically different from placebo (−0.03±0.16 vs. 0.05±0.23, P=0.2).

Body fat mass was reduced by CLA compared to placebo as measured by DXA (CLA 0.8±1.4 kg vs. placebo 1.8±1.3 kg, P=0.01). When taken as a percentage of total body weight, body fat percentage was reduced by CLA compared to placebo (−0.5±2.1 vs. 1.3±1.8%, P=0.001). Abdominal body fat as a percentage of total body weight was decreased by CLA (−0.09±0.86 vs. 0.43±0.59%, P=0.02). Peripheral fat (including arms and legs) as a percentage of total body weight was decreased by CLA (−1.21±0.96 vs. 0.53±1.22%, P≤0.001). Increase in bone mineral content (head excluded) over 6 months as measured by DXA was less in the CLA group than placebo group. (CLA 0.05±0.03, placebo 0.07±0.03 kg, P=0.04).

The above analyses were completed using a priori inclusion criteria; however, the differences were also analyzed by intent to treat with the last measure carried forward. Thus there was zero change for those who did not return for the 6-month measures. The outcomes that remained significant based on intent to treat were fat mass (P=0.02) and body fat percentage (P=0.002)

The results indicate that CLA supplementation has an effect on fat gain during pre-pubertal growth. Compared to placebo, CLA significantly reduced total body fat gain in a 6-month trial, and regionally reduced the percentage of abdominal fat and peripheral fat as a percentage of total body weight. BMI also improved during the 6-month supplementation period.

As indicated above, CLA reduced the rate of increase in BMI compared to placebo. The change in BMI observed, however, was still faster than the 0.3 and 0.2 kg/m$^2$ expected in 6 months for boys and girls based on the 50$^{th}$ percentile of the 2001 NCHS growth charts, but were similar to the 95 percentile values of 0.5 and 0.6 kg·m$^2$ for 6 months in boys and girls respectively. Weight changes were not different between treatments, but both were similar to the 2 and 3 kg gains expected for the 95 percentile for this age group of boys and girls, respectively. This is still greater than the 1.5 and 2. kg expected at the 50$^{th}$ percentile. Thus, although CLA had a positive effect on the increase in BMI, the rates of increase did not appear to return to the 50$^{th}$ percentile averages for age. The composition of weight gain, however, was only 25% fat in the CLA group compared to 49% fat in the placebo group. As such, CLA treatment almost normalized the percentage of fat in weight gain which was estimated to be 15% and 24% in 8 year boys and girls, respectively.

In conclusion, we found that supplementation of 80% of pure CLA containing equal amounts c9t11 and t10c12 CLA to be effective in reducing body fat accretion and percent body fat of overweight, prepubescent, generally healthy children.

The invention claimed is:

1. A method of treating childhood obesity comprising:
   administering an effective amount of conjugated linoleic acid (CLA) or a derivative thereof to a growing child;
   wherein the derivative is selected from the group consisting of a free acid, a physiologically acceptable salt of the free acid, an ester, and a triglyceride; and
   wherein an effective amount reduces a rate of increase of fat mass in the growing child.

2. The method of claim 1, wherein the growing child is 4 to 18 years of age.

3. The method of claim 2, wherein the growing child is 4 to 16 years of age.

4. The method of claim 3, wherein the growing child is 5 to 12 years of age.

5. The method of claim 4, wherein the growing child is 6 to 10 years of age.

6. The method of claim 1, wherein the child is human.

7. The method of claim 1, wherein the child is an age at which the body mass index (BMI) for the 50$^{th}$ percentile is increasing with age.

8. The method of claim 1, wherein the child's weight increases.

9. The method of claim 1, wherein the CLA is a free acid.

10. The method of claim 1, wherein the CLA is a triglyceride.

11. The method of claim 1, wherein the CLA is a mixture of two or more different isomers.

12. The method of claim 11, wherein the mixture comprises trans10, cis12 and cis9, trans11 isomers of CLA.

13. The method of claim 12, wherein the trans10, cis12 isomer to cis9, trans 11 weight ratio is at least 1.2:1.

14. The method of claim 13, wherein the weight ratio is 1.3:1.

15. The method of claim 13, wherein the weight ratio is 1.5:1.

16. The method of claim 13, wherein the weight ratio is 1.5:1 to 10:1.

17. The method of claim 13, wherein the weight ratio is 1.5:1 to 100:1.

18. The method of claim 11, wherein the mixture comprises at least 30 wt % cis9, trans11 isomer and at least 30 wt % trans10, cis12 isomer.

19. A method of treating childhood obesity comprising:
   administering a pharmaceutical composition comprising an effective amount of conjugated linoleic acid (CLA) or a derivative thereof to a growing child;
   wherein the derivative is selected from the group consisting of a free acid, a physiologically acceptable salt of the free acid, an ester, and a triglyceride; and
   wherein an effective amount reduces a rate of increase of fat mass in the growing child.

20. The method of claim 19, wherein the pharmaceutical composition is selected from the group consisting of a tablet, pill, capsule, caplet, multiparticulate, powder, elixir, syrup, suspension, and solution.

21. The method of claim 20, wherein the multiparticulate is selected from the group consisting of granules, beads, pellets, and micro-encapsulated particles.

22. The method of claim 19, wherein the pharmaceutical composition further comprises a pharmaceutically acceptable diluent or carrier.

23. The method of claim 20, wherein the pharmaceutical composition further comprises one or more of flavoring agents, coloring agents, sweeteners, emulsifiers, and combinations thereof.

24. The method of claim 19, wherein the pharmaceutical composition is a dosage unit of 1 mg to 1000 mg.

25. The method of claim 24, wherein the dosage unit to 100 mg to 750 mg.

26. A method of treating childhood obesity comprising:
   administering a food supplement comprising an effective amount of conjugated linoleic acid (CLA) or a derivative thereof to a growing child;
   wherein the derivative is selected from the group consisting of a free acid, a physiologically acceptable salt of the free acid, an ester, and a triglyceride; and wherein an effective amount reduces a rate of increase of fat mass in the growing child.

27. The method of claim 26, wherein the food supplement is a soft gel or hard capsule.

28. The method of claim 27, wherein the food supplement comprises an encapsulating material selected from the group consisting of gelatin, glycerol, starch, modified starch, and starch derivatives.

29. The method of claim 28, wherein the starch derivative is glucose, sucrose, lactose, or fructose.

30. The method of claim 28, wherein the encapsulating material further comprises cross-linking agents, polymerizing agents, stabilizers, antioxidants, light absorbing agents, or preservatives.

31. The method of claim 26, wherein the food supplement comprises 1 mg to 1000 mg CLA or derivative thereof.

32. The method of claim 26, wherein the food supplement comprises 100 mg to 750 mg CLA or derivative thereof.

* * * * *